US012667535B2

(12) United States Patent
Brossard et al.

(10) Patent No.: US 12,667,535 B2
(45) Date of Patent: Jun. 30, 2026

(54) COSMETIC COMPOSITION HAVING GLOSS AND LASTING PROPERTIES

(71) Applicant: L V M H RECHERCHE, Saint-Jean de Brave (FR)

(72) Inventors: Fabienne Brossard, Saint-Jean de Brave (FR); Mathilde Garnier, Saint-Jean de Brave (FR); Valérie Bouchard De La Poterie, Saint Jean de Brave (FR)

(73) Assignee: L V M H RECHERCHE, Saint-Jean de Brave (FR)

( * ) Notice: Subject to any disclaimer, the term of this patent is extended or adjusted under 35 U.S.C. 154(b) by 416 days.

(21) Appl. No.: 17/787,206

(22) PCT Filed: Dec. 18, 2020

(86) PCT No.: PCT/FR2020/052535

§ 371 (c)(1),
(2) Date: Jun. 17, 2022

(87) PCT Pub. No.: WO2021/123667

PCT Pub. Date: Jun. 24, 2021

(65) Prior Publication Data

US 2023/0033961 A1 Feb. 2, 2023

(30) Foreign Application Priority Data

Dec. 20, 2019 (FR) ...................................... 1915241

(51) Int. Cl.

| | |
|---|---|
| ***A61K 8/891*** | (2006.01) |
| ***A61K 8/02*** | (2006.01) |
| ***A61K 8/34*** | (2006.01) |
| ***A61K 8/73*** | (2006.01) |
| ***A61K 8/81*** | (2006.01) |
| ***A61Q 1/06*** | (2006.01) |

(52) U.S. Cl.

CPC ............ *A61K 8/891* (2013.01); *A61K 8/0229* (2013.01); *A61K 8/342* (2013.01); *A61K 8/73* (2013.01); *A61K 8/8147* (2013.01); *A61K 8/8182* (2013.01); *A61Q 1/06* (2013.01); *A61K 2800/31* (2013.01); *A61K 2800/43* (2013.01)

(58) Field of Classification Search

CPC ...... A61K 8/891; A61K 8/0229; A61K 8/342; A61K 8/73; A61K 8/8147; A61K 8/8182; A61K 2800/31; A61K 2800/43; A61K 8/31; A61K 8/8152; A61K 8/8158; A61K 8/817; A61Q 1/06; A61Q 1/04; A61Q 8/0216

See application file for complete search history.

(56) References Cited

U.S. PATENT DOCUMENTS

| | | | | |
|---|---|---|---|---|
| 2008/0102049 | A1* | 5/2008 | McDermott | A61K 8/4913 525/440.03 |
| 2010/0092409 | A1* | 4/2010 | Amin | A61K 8/64 424/59 |
| 2012/0294816 | A1* | 11/2012 | Kawaratani | A61K 8/8111 424/78.03 |
| 2019/0015314 | A1 | 1/2019 | Lahousse et al. | |

FOREIGN PATENT DOCUMENTS

| | | | |
|---|---|---|---|
| JP | 2016-117701 A | | 6/2016 |
| JP | 2016190810 A | * | 11/2016 |
| WO | WO-2015/014789 A1 | | 2/2015 |

OTHER PUBLICATIONS

"Lip Science: What's Different about the Skin on Your Lips? 2018".*

Ashland Care Specialties Advancing skin care with science Jul. 2018 (wayback machine).*

International Search Report and Written Opinion for Corresponding International Application No. PCT/FR2020/052535, mailing date May 14, 2021.

Search Report, French Application No. FA 875871 and FR 1915241, dated Aug. 4, 2020.

Mintel, "Liquid Rouge Bijou" Line of Ingredients, www.gnpd.com Jul. 30, 2019.

Japanese Office Action for Japanese Application No. 2022-537865, dated Feb. 4, 2025, with English translation.

* cited by examiner

*Primary Examiner* — Jessica Worsham

(74) *Attorney, Agent, or Firm* — Birch, Stewart, Kolasch & Birch, LLP

(57) ABSTRACT

The invention relates to a cosmetic composition comprising, in a physiologically acceptable medium, an oily phase and at least a) a phenyl silicone oil of formula (I) [Chem 1] (I) wherein—Me is methyl and Ph is phenyl, OR' represents an —OSiMe3 group, —y ranges from 1 to 1000, and—z ranges from 1 to 1000, b) a C8-C30 fatty alcohol, c) a branched dextrin ester, and d) advantageously a liposoluble polymer selected from among the group consisting of: (i) acrylate polymers selected from among the group consisting of silicone acrylate polymers, acrylate polymers comprising an alkyl chain of at least 10 carbon atoms, and copolymers of acrylates and acrylamide, (ii) copolymers of vinylpyrrolidone (VP) and alkene comprising at least 18 carbon atoms, and (iii) mixtures thereof, and its use in particular on the lips for a make-up result with improved gloss and longer-lasting gloss and color. Preferably, the composition is in a semi-solid or solid form.

10 Claims, No Drawings

COSMETIC COMPOSITION HAVING GLOSS AND LASTING PROPERTIES

CROSS REFERENCE TO RELATED APPLICATIONS

This application is a U.S. National Stage of International Patent Application No. PCT/FR2020/052535 filed Dec. 18, 2020, which claims the benefit of priority of French Patent Application No. 1915241 filed Dec. 20, 2019, the respective disclosures of which are each incorporated herein by reference in their entireties.

FIELD OF THE INVENTION

The present invention relates to the field of cosmetics and in particular to a cosmetic composition having gloss and long-lasting gloss properties.

PRIOR ART

Makeup products for lips are known in the prior art in liquid, semi-liquid or solid (stick) form having colour long-lasting properties. Also, gloss makeup products for the lips are also known, but it is difficult to combine gloss properties and gloss long-lasting properties, even more so in one and the same composition.

“Two-step” lip makeup products are effectively known whereby a first composition is applied to provide colour and a second composition is applied to deposit a glossy film. However, there still subsists a need to develop compositions for application that is both simple and faster, in a single step, allowing the imparting both of improved gloss properties and of long-lasting colour and gloss properties, whilst remaining comfortable.

The Applicant has precisely evidenced that the combined use of two non-miscible oils, of a particular resin and of particular polymers for long-wear, allows this need to be met. The present invention, through the formation of a transparent surface film resulting from demixing of two non-miscible oils, therefore allows immediate gloss to be obtained equal to or greater than that of lip glosses available on the market, with improved gloss lasting properties. The invention also affords colour-lasting and colour transfer-resistant properties that are particularly remarkable, due to the formation of a transparent film on the surface of the film applied to the lips.

The composition of the invention is a homogeneous composition which can be in liquid, semi-solid or solid form. More especially, it is a lip makeup composition for one-step application.

DISCLOSURE OF THE INVENTION

It is one objective of the invention to propose a care and/or makeup composition for keratin material, in particular a one-step makeup composition for the lips, having improved gloss and gloss lasting properties.

For this purpose, in a first aspect of the invention, there is proposed a cosmetic composition comprising, in a physiologically acceptable medium, an oily phase and at least:

a) a phenyl silicone oil of formula (I)

[Chem 1]

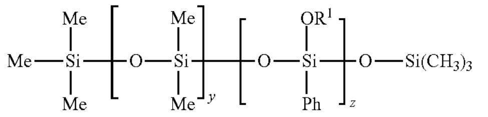

(I)

where:

Me is methyl and Ph is phenyl, OR' represents an —$OSiMe_3$ group, y ranges from 1 to 1000, and z ranges from 1 to 1000, b) a C8-C30 fatty alcohol, c) a branched dextrin ester, and d) advantageously a liposoluble polymer selected from the group formed by:

(i) acrylate polymers selected from the group formed by silicone acrylate polymers, acrylate polymers comprising an alkyl chain of at least 10 carbon atoms and copolymers of acrylates and acrylamide, (ii) copolymers of vinylpyrrolidone (VP) and alkene having at least 18 carbon atoms, and (iii) mixtures thereof.

The composition of the invention is a homogeneous composition. By ‘homogeneous’, it is meant that the composition of the invention has the same characteristics and/or the same properties in every part thereof.

The composition of the invention particularly has a homogeneous or uniform visual appearance i.e. each of the phases it comprises cannot be individualised by the naked eye, as opposed to a ‘multiphase or biphasic’ composition in which the phases can be distinguished by the naked eye, or in which parts can be seen not having the same characteristics and/or same properties.

This homogeneous and stable appearance is characteristic of the composition when in bulk or unit packaging form. On the other hand, when applied to keratin material, the coexistence of non-miscible oils in the composition produces oil demixing and the formation of a transparent film on the surface of the makeup film applied to the keratin material.

The homogeneity and stability of the composition of the invention are generally reached through the use of a fatty phase texturizing agent such as a pasty fatty substance, wax, polymer or any gelling or thickening agent soluble or dispersed in the fatty phase, or mixtures thereof. In particular, the texturizing agent can be selected from among a wax, pasty fatty substance or mixture thereof.

As a function of the total content of texturizing agent(s), the composition of the invention can have greater or less viscosity. The total content of texturizing agent(s) in the composition of the invention generally ranges from 3% to 15% by weight relative to the total weight of the composition. For the lowest values (close to 3%), the composition of the invention can be in fluid form, of homogeneous appearance, slightly viscous. The composition of the invention can also be in semi-solid form, even in solid form, with higher contents of texturizing agents.

In one particular and preferred embodiment, the composition is in semi-solid or solid form at 20° C. and at atmospheric pressure.

By ‘semi-solid’, it is meant a composition having a consistency or texture which is neither liquid i.e. it does not flow spontaneously under its own weight at 20° C. and at atmospheric pressure (760 mm de Hg), nor solid since it has a hardness of less than 30 $Nm^{-1}$.

By 'solid', it is meant a composition having hardness, at a temperature of 20° C. and at atmospheric pressure (760 mm de Hg), greater than 30 $Nm^{-1}$, preferably greater than 40 $Nm^{-1}$. Hardness can be measured at 20° C. with the so-called «butter wire cutter» method, whereby a stick of product, preferably of cylindrical revolution, is cut cross-wise with a rigid metal wire of diameter 250 μm, the wire in relation the stick being moved at a rate of 60 mm/min. The hardness of samples is expressed in g and can be measured using a texture analyzer of Texturometre TAXT Plus type.

The semi-solid or solid texture of the composition not only allows the production of special shapes e.g. sticks, but also allows the homogeneity of the composition to be further improved in bulk or unit packaging form, whilst permitting oil demixing and the formation of a transparent film on the surface of the film applied to the lips all at the same time.

The invention also concerns a cosmetic method comprising the application to keratin material and in particular to the skin and/or lips, preferably the lips, of a composition such as defined in the invention.

In particular, the composition is a makeup composition and preferably a makeup composition for the lips.

DETAILED DESCRIPTION OF THE INVENTION

A first subject of the invention concerns a cosmetic composition comprising, in a physiologically acceptable medium, an oily phase and at least:

a) a phenyl silicone oil of formula (I)

[Chem 1]

(I)

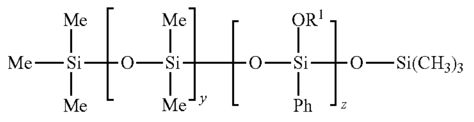

where:

Me is methyl and Ph is phenyl, OR' represents an $—OSiMe_3$ group, y ranges from 1 to 1000, and z ranges from 1 to 1000, b) a C8-C30 fatty alcohol, c) a branched dextrin ester, and d) advantageously a liposoluble polymer selected from the group formed by:

(i) acrylate polymers selected from the group formed by silicone acrylate polymers, acrylate polymers comprising an alkyl chain of at least 10 carbon atoms and copolymers of acrylates and acrylamide.

(ii) copolymers of vinylpyrrolidone (VP) and alkene having at least 18 carbon atoms, and (iii) mixtures thereof.

In one particular and preferred embodiment, the composition also comprises a texturizing, gelling and/or structuring agent, in particular pasty fatty substances, waxes or mixture thereof, which allow stabilizing, and even binding, the system without perturbing the result of gloss and lasting power.

Therefore, in one particular and preferred embodiment, the composition of the invention comprises a pasty fatty substance, a wax or mixture thereof, and preferably in a total amount ranging from 3 to 15% by weight relative to the total weight of said composition.

In one embodiment of the invention, the composition of the invention is in the form of a homogeneous fluid composition when in bulk or unit packaging form.

In another embodiment, the composition of the invention is in the form of a semi-solid composition.

In a further embodiment, the composition of the invention is in the form of a solid composition.

Preferably, it is a semi-solid or solid composition, and more preferably a solid composition.

The C8-C30 fatty alcohol and branched dextrin ester are chosen to allow adhering of colour to keratin material. The phenyl silicone oil, non-miscible with the C8-C30 fatty alcohol, forms an ultra-glossy transparent surface film.

To improve comfort on application and for long-lasting comfort, oils and semi-solid fatty substances can advantageously be added. To improve lasting properties and/or to reduce feelings of tackiness which may progressively become apparent due to the presence of the branched ester and other optional long-wear polymers, powder fillers can advantageously be added. To increase glide-on application and improve sensorial performance of the deposited film, additional oils which self-eliminate on application and film formation can also be added.

To increase the long-wear properties of gloss and colour (in other words non-transfer properties), polymers are advantageously added.

The composition of the invention therefore comprises at least one oily phase.

By «oily phase» it is meant an oil or mixture of oils.

By «oil», in the invention it is meant a fatty substance that is not water-soluble, liquid at 25° C. and at atmospheric pressure.

An oily phase in the invention may comprise hydrocarbon, silicone oils and mixtures thereof.

By 'silicone oil' in the invention, it is meant an oil comprising at least one silicon atom and in particular at least one Si—O group.

By 'hydrocarbon oil' in the invention, it is meant an oil chiefly containing hydrogen and carbon atoms.

The composition of the invention particularly comprises at least one phenyl silicone oil and one hydrocarbon oil.

Phenyl Silicone Oil

The composition of the invention comprises at least one phenyl silicone oil. By 'phenyl silicone oil' in the invention it is meant an organopolysiloxane substituted by at least phenyl group.

The phenyl silicone oil of the invention is selected in particular from the group formed by phenyl trimethicones, phenyl dimethicones, phenyl trimethylsiloxy diphenylsiloxanes, diphenyl dimethicones, diphenyl methyldiphenyl trisiloxanes, 2-phenylethyl trimethylsiloxysilicates, trimethyl pentaphenyl trisiloxane, and mixtures thereof.

In one particular embodiment, the composition of the invention comprises a phenyl silicone oil of formula (I)

[Chem 1]

(I)

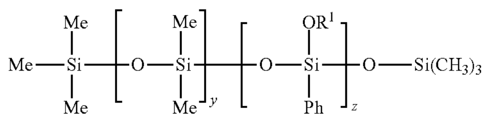

where Me is methyl and Ph is phenyl, OR' represents an —$OSiMe_3$ group and y ranges from 1 to 1000, z ranges from 1 to 1000.

For example, use can be made of Belsils PDM20, PDM100 and PDM1000 by Wacker, and in particular of trimethyl siloxyphenyl dimethicone sold under the trade name BELSIL PDM 1000 and marketed by Wacker (MW=9000 g/mol).

The non-volatile phenyl silicone oil is contained in the composition of the invention in an amount ranging from 10 to 40% by weight, in particular 15 to 35% by weight relative to the total weight of said composition.

In one particular and preferred embodiment, the composition of the invention comprises at least one phenyl silicone oil of formula (I), preferably an oil having the INCI name trimethyl siloxyphenyl dimethicone.

The composition may also comprise a second phenyl silicone oil differing from the first and having formula (II):

[Chem 2]

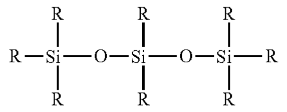

where the R groups are each independently a methyl or phenyl, at least three thereof, even at least four thereof, even at least five thereof being a phenyl.

In one particular embodiment, the composition of the invention, as second non-volatile phenyl silicone oil, comprises a compound of formula (III):

[Chem 3]

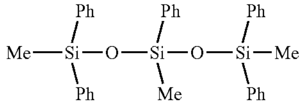

where Me is a methyl and Ph is a phenyl, otherwise called trimethyl pentaphenyl trisiloxane.

Said phenyl silicone is produced in particular by Dow Corning under reference PH-1555 HRI or Dow Corning 555 Cosmetic Fluid (chemical name: 1,3,5-trimethyl 1,1,3,5,5-pentaphenyl trisiloxane, INCI name: trimethyl pentaphenyl trisiloxane). The reference Dow Corning 554 Cosmetic Fluid can also be used. In one preferred embodiment, use is made of the reference PH-1555 HRI (INCI name: trimethyl pentaphenyl trisiloxane).

In one particular embodiment, the second phenyl silicone oil differing from the first phenyl silicone oil described above is contained in an amount ranging from 2 to 12% by weight, in particular 4 to 10% by weight relative to the total weight of the composition.

In one particular embodiment, the first and second phenyl silicone oils are contained in the composition in a weight ratio (% $1^{st}$ non-volatile phenyl silicone oil: % $2^{nd}$ non-volatile phenyl silicone oil) ranging from 2 to 6, in particular from 3 to 5.

C8-C30 Fatty Alcohols (Oil Non-Miscible with the Phenyl Silicone Oil)

The compositions of the invention also comprise at least one fatty alcohol. The fatty alcohols can be represented by the formula ROH, R being a linear or branched, saturated or unsaturated hydrocarbon radical having at least 8 carbon atoms, more particularly having 8 to 30 carbon atoms.

In one embodiment, the above-mentioned radical R is a linear or branched, saturated or unsaturated hydrocarbon radical having 8 to 30, in particular 10 to 24 and preferably 12 to 22 carbon atoms.

As examples of fatty alcohols able to be used in the invention, mention can be made of linear or branched fatty alcohols, of synthetic or natural origin. Evidently, other long chain alcohols can also be used e.g. ether-alcohols or so-called Guerbet alcohols.

In one particular embodiment, the C8-C30 fatty alcohol is selected from the group formed by lauric alcohol, myristic alcohol, isostearyl alcohol, palmitic alcohol, oleic alcohol, behenic alcohol, erucic alcohol, arachidyl alcohol, 2-butyloctanol, 2-undecyl pentadecanol, 2-hexyldecyl alcohol, isocetyl alcohol, octyldodecanol and mixtures thereof.

Preferably, use is made of octyldodecanol. ISOFOL 20 by SASOL can particularly be cited.

In one particular embodiment, the amount of fatty alcohol in the composition of the invention rages from 1% to 10% by weight relative to the total weight of said composition, preferably 2% to 5% by weight relative to the total weight of said composition for a solid formula.

In one particular embodiment, the composition comprises at least one first phenyl silicone oil such as previously described and at least one C8-C30 fatty alcohol in a weight ratio (R1=% non-volatile phenyl silicone oil: % C8-C30 fatty alcohol) ranging from 8 to 20, in particular from 10 to 18.

In one particular embodiment, the composition comprises at least one first phenyl silicone oil and a second phenyl silicone oil such as previously described and at least one C8-C30 fatty alcohol in a weight ratio (R2=(% $1^{st}$ phenyl silicone oil+% $2^{nd}$ phenyl silicone oil): C8-C30 fatty alcohol) ranging from 12 to 25, in particular from 15 to 20.

Branched Dextrin Ester (Film-Forming Agent)

The branched dextrin ester of the invention may comprise an esterified chain or several esterified chains, the same or different. For example, it may be a dextrin esterified by several same or different fatty acids. These dextrin esters can be prepared by implementing convention esterification methods. For example, the following methods can be implemented:

1) Dextrin having an average degree of polymerization of glucose of 3 to 150 is reacted with one or more derivatives of branched fatty acids, and optionally with one or more derivatives of other fatty acids, in required proportions to obtain the previously described dextrin ester.
2) Dextrin having an average degree of polymerization of glucose of 3 to 150 is reacted at a first step with one or more derivatives of branched fatty acids, then at a second step with one or more derivatives of one or more of other fatty acids, in required proportions to obtain the previously described dextrin ester. Use is usually made of halides, acid anhydrides as fatty acid derivatives. More particularly, in one or other of the two aforementioned options, the dextrin is dispersed in a reaction solvent, and a catalyst is added thereto if necessary. This mixture is caused to react through the addition of the aforementioned derivative(s) of fatty acids, preferably halides.

In method 1), these derivatives are mixed and simultaneously added to the reaction mixture and in method 2) the derivatives are successively added. As usual solvent, mention can be made of dimethylformamide, formamide, acetamide, ketones, aromatic compounds such as benzene, toluene, le xylene, dioxane, or mixtures thereof. Suitable catalysts are usually selected from among tertiary amino compounds such as pyridine, picoline. The reaction temperature is generally chosen as a function of the starting derivatives of the fatty acid(s). It is generally between 0 and 100° C. The dextrin esters are then purified in usual manner.

In one particular embodiment, the branched dextrin ester is a dextrin ester for which dextrin has an average degree of polymerization of glucose of 3 to 150, and for which the fatty acid(s) comprise from 50 to 100 mole %, on the basis of the total quantity of fatty acid(s), of one or more branched saturated fatty acids having 4 to 26 carbon atoms, and from 0 to less than 50 mole %, on the basis of the total quantity of fatty acid(s), of one or more other fatty acids selected from the group formed by linear saturated fatty acids having 2 to 22 carbon atoms, linear or branched saturated fatty acids having 6 to 30 carbon atoms, and the saturated or unsaturated cyclic fatty acids having 6 to 30 carbon atoms, and for which the degree of substitution of dextrin by the fatty acid(s) is from 1.0 to 3.0 per glucose unit.

Said dextrin esters are particularly described in European application EP 2537865.

In one preferred embodiment, the branched dextrin ester is selected from among dextrin isostearate, dextrin isoarachidate, dextrin isopalmitate, dextrin isononanoate and mixtures thereof.

Preferably, the branched dextrin ester is dextrin isostearate.

Among marketed compounds, mention can be made of UNIFILMA HVY dextrin isostearate marketed by Chiba Flour Milling Co.

In one embodiment, the branched dextrin ester is contained in the composition in an amount ranging from 5% to 25% by weight relative to the total weight of the composition.

More particularly, the percentage of branched dextrin ester is between 10% and 20% by weight relative to the total weight of the composition, further particularly between 12% and 18% by weight relative to the total weight of said composition.

Liposoluble Polymer (Long-Wear Polymer)

The composition of the invention also advantageously comprises a liposoluble polymer selected from the group formed by:

(i) acrylate polymers selected from the group formed by silicone acrylate polymers, acrylate polymers comprising an alkyl chain of at least 10 carbon atoms and copolymers of acrylates and acrylamide, (ii) copolymers of vinylpyrrolidone (VP) and alkene having at least 18 carbon atoms, and (iii) mixtures thereof.

The liposoluble polymer can be a polymer intended to provide long-wear and/or to form a film (so-called «film-forming» polymer).

By film-forming polymer it is meant a polymer able to form a continuous film on a substrate. Herein, the word polymer can designate a homopolymer or copolymer. By «copolymer», it is meant a polymer comprising at least two different monomers or two different blocks, possibly from the same chemical family but of different structure. By liposoluble film-forming polymer, it is meant a film-forming polymer solubilized in the liquid fatty phase, for example in the phenyl silicone oil of the invention.

The film-forming polymer can be or natural or synthetic origin.

The acrylate polymers used in the present invention act as long-wear polymers and the copolymers of vinylpyrrolidone (VP) and alkene having at least 18 carbon atoms act as film-forming polymers.

Acrylate Polymers

The acrylate polymers able to be used in the composition of the invention are advantageously selected from among:

- silicone acrylate polymers, in particular acrylate/dimethicone copolymers and especially acrylate/dimethicone copolymers in cyclopentasiloxane (for example KP-545 by Shin-Etsu), acrylate/dimethicone copolymers in methyl trimethicone (for example KP-549 and KP-579 by Shin-Etsu), and acrylate/dimethicone copolymers in isododecane (for example KP-550 by Shin-Etsu); acrylate/polytrimethylsiloxy-methacrylate copolymers and in particular acrylate/polytrimethylsiloxy-methacrylate copolymers in dimethicone (for example FA-4003 DM by Dow Corning®), acrylate/polytrimethylsiloxy-methacrylate copolymers in isododecane (for example FA-4004 ID by Dow Corning®), acrylates/stearyl acrylate/dimethicone methacrylate copolymers such as KP-561P by Shin Etsu);
- acrylate polymers comprising an alkyl chain of at least 10 carbon atoms, in particular C10-C30 acrylate (homo) polymers having the INCI name: poly C10-30 alkyl acrylates, such as the one marketed under the trade name TEGO SP 13-1 by AIR PRODUCTS; and
- copolymers of acrylates and acrylamide, in particular the copolymers of acrylates and t-butylacrylamides, such as the one marketed under the trade name ULTRAHOLD 8 or ULTRAHOLD STRONG (INCI: «Acrylates/t-Butylacrylamide copolymer) by BASF. In one particular embodiment, the copolymer of acrylate and acrylamide is pre-dispersed in a non-volatile oil to facilitate integration thereof into the oily phase of the composition, in particular a hydrogenated polyisobutene.

The acrylate polymers used in the composition of the invention are contained in an amount ranging from 1 to 10% by weight, in particular 2 to 6% by weight relative to the total weight of said composition.

Copolymers of Vinylpyrrolidone (VP) and Alkene

The copolymers of vinylpyrrolidone (VP) and alkene able to be used in the composition of the invention comprise an alkene chain of at least 18 carbon atoms, in particular a C18-C30 alkene chain such as the copolymers VP/eicosene, VP/triacontanyl.

Preferably, use is made of the vinylpyrrolidone (VP) copolymers comprising a C20-C30 linear alkene chain such as VP/eicosene marketed under the trade name ANTARON V 220 F (INCI: eicosene vinylpyrrolidone copolymer) by ASHLAND, triacontanyl PVP marketed under the trade name UNIMER U-6 by INDUCHEM.

The VP and alkene copolymers used in the composition of the invention are contained in an amount ranging from 8 to 20% by weight, in particular 10 to 15% by weight relative to the total weight of said composition.

In one particular and preferred embodiment, the composition of the invention comprises at least one C18-C30 copolymer of VP and alkene such as previously described, in particular a VP/eicosene copolymer marketed under the trade name ANTARON V 220 F (INCI: eicosene vinylpyrrolidone copolymer) by Ashland.

In another particular embodiment, the composition of the invention comprises an acrylate polymer such as previously defined and a C18-C30 copolymer of VP and alkene such as previously described.

In this particular embodiment, the weight ratio between the acrylate polymer and C18-C30 VP/alkene copolymer (R=% acrylate polymer/% C18-C30 VP/alkene copolymer) ranges from 1 to 5, in particular from 2 to 4.

In another particular embodiment, the composition of the invention comprises a liposoluble film-forming polymer selected from among a copolymer of acrylates and acrylamide and a copolymer of vinylpyrrolidone (VP) and alkene having at least 20 carbon atoms, preferably selected from among a copolymer of acrylate and t-butylacrylamide and a copolymer of vinylpyrrolidone (VP) and eicosene, and preferably a mixture thereof.

The total content of liposoluble film-forming polymers in the composition of the invention can range from 8 to 25% by weight, in particular from 10 to 20% by weight relative to the total weight of said composition. The % of liposoluble film-forming polymer is expressed in weight % of active material (a.m) relative to the total weight of the composition.

In one particular and preferred embodiment, the composition of the invention comprises at least the following ingredients:

trimethylsiloxyphenyl dimethicone
octyldodecanol
dextrin isostearate
and a VP/eicosene copolymer.

In one particular and preferred embodiment, the composition of the invention comprises at least the following ingredients:

trimethyl pentaphenyl trisiloxane
octyldodecanol
dextrin isostearate
an acrylate/t-butylacrylamide copolymer
and advantageously a VP/eicosene copolymer.

The fatty phase of the composition of the invention is generally texturized or structured by a texturizing agent, in particular a wax, pasty fatty substance, or mixture thereof.

Therefore, in one particular and preferred embodiment, the composition of the invention comprises a pasty fatty substance, a wax or mixture thereof, and preferably in a total amount ranging from 3 to 15% by weight relative to the total weight of said composition.

Waxes

Therefore, in one particular and preferred embodiment, the composition of the invention additionally comprises at least one wax allowing stabilization, even binding, of the system without perturbing the result of long-wear and gloss.

By wax in the invention, it is meant to designate a compound solid at 25° C. having reversible change in solid/liquid state and a melting point higher than 30° C., preferably higher than 45° C.

Natural waxes can be cited (sunflower seed wax, berry wax) as well as microcrystalline waxes, paraffin waxes, polyethylene waxes, ozokerite, carnauba wax, beeswax, products comprising a mixture of polyethylene and alcohols having 20 to 50 carbon atoms, silicone waxes and in particular alkyl dimethicones, C20-C40 alkyl stearates, waxes obtained by catalytic hydrogenation of vegetable oils having C8-C32 linear or branched chains such as hydrogenated jojoba oil, waxes obtained by hydrogenation of castor oil esterified with a fatty alcohol, candelilla wax, copolymers of maleic anhydride and alpha-olefin, waxes obtained by metallocene catalysis and lanolin wax.

In one particular embodiment, the cosmetic composition of the invention comprises at least one candelilla wax.

A composition of the invention may have a wax content ranging from 2 to 20%, for example 3 to 15% by weight, relative to the total weight of the composition.

Therefore, in one particular and preferred embodiment, the invention concerns a cosmetic composition comprising 3% to 15% by weight of waxes relative to the total weight of said composition.

Pasty Fatty Substance

In one particular embodiment, the composition of the invention may comprise a pasty fatty substance.

By «pasty fatty compound» or «pasty compound» or «pasty fatty substance», it is meant to designate a non-crystalline fatty compound having, at a temperature of 25° C., a liquid fraction and a solid fraction.

The pasty compound is selected for example from the group formed by the triglycerides of fatty acids and derivatives thereof, shea butter, cocoa butter, mango oil or butter, and mixtures thereof.

In particular, the pasty compound is selected from among the triglycerides of fatty acids and derivatives thereof, such as caprylic/capric/myristic/stearic triglycerides.

A composition of the invention may have a content of pasty compounds ranging from 1% to 10%, for example 2% to 6% by weight, relative to the total weight of the composition.

In one particular embodiment, the composition of the invention further comprises an additional ingredient selected from among oils, fillers, pasty fatty substances, coloring materials, and mixtures thereof.

Other Additional Oils

The invention may further comprise other silicone or hydrocarbon oils, differing from the previously described oils, to impart lightweight and long-wear to the film deposited on the skin.

These oils self-eliminate spontaneously at the time of application and formation of the film on the lips. These oils can particularly be chosen from among 0.5 to 6 cSt dimethicones, $C_8$-$C_{16}$ branched alkanes, $C_9$-$C_{15}$ linear alkanes, $C_8$-$C_{16}$ branched esters and mixtures thereof.

In one preferred embodiment, the oil is selected from among $C_8$-$C_{16}$ branched alkanes, in particular it is isododecane, or $C_9$-$C_{13}$ linear alkanes.

As examples of linear alkanes suitable for the invention, mention can be made of n-nonane (C9), n-decane (C10), n-undecane (C11), n-dodecane (C12), n-tridecane (C13), and mixtures thereof. In one particular embodiment, the volatile linear alkane is selected from among n-nonane, n-undecane, n-dodecane, n-tridecane, n-tetradecane, and mixtures thereof. In one preferred embodiment, the mixtures can be cited of n-undecane (C11) and n-tridecane (C13) such as those sold under the trade name CETIOL by BASF, and the mixtures of n-dodecane (C12) and n-tetradecane (C14) such as those sold under the trade name VEGELIGHT by GRANT INDUSTRIES, and mixtures thereof.

In one particular embodiment, these oils can be contained in the composition in a total amount ranging from 2 to 20% by weight, in particular 4 to 15% by weight relative to the total weight of said composition.

Fillers

In addition, the composition of the invention may advantageously comprise fillers to reduce the feel of tackiness which may gradually occur on the lips due to the presence of the branched dextrin ester.

In the meaning of the invention, by «fillers» it is to be understood particles of any shape, white or colourless, of mineral or organic, natural or synthetic type, having a form (flake, spherical or oblong) that is insoluble and dispersed in the medium of the composition. The fillers are selected in particular from among silicas, micas of natural or synthetic origin, kaolin, zinc and titanium oxides; calcium carbonate, magnesium carbonate and hydrogen carbonate; zinc, magnesium or lithium stearates, zinc laurate, magnesium myristate; the powders of synthetic polymers such as polyethylene, polyesters, polyamides (e.g. nylon); powders of polyacrylic or polymethacrylic acids, powders of silicone or silicone resin; cellulose powders; mineral powders such as spherical silica; spherical titanium dioxides; glass and ceramic beads; powders of organic materials of natural origin such as starches of corn, wheat, rice, whether or not crosslinked, and mixtures thereof.

As preferred fillers, particular mention can be made of cellulose powders, silicon powders in particular the powders having the INCI name silicon dioxide, and mixtures thereof.

The fillers can be contained in an amount ranging from 2 to 20%, in particular 3 to 15% by weight relative to the total weight of the composition.

A composition of the invention is in particular a makeup composition comprising at least one coloring material.

Coloring Materials

By coloring material in the present invention, it is meant a compound able to produce a coloured optical effect when formulated in sufficient amount in a suitable cosmetic medium.

A coloring material can be selected from among coloring materials which may or may not be water-soluble, liposoluble or non-liposoluble, organic or inorganic, materials having an optical effect, and mixtures thereof.

In one particular embodiment, the coloring materials are particularly selected from among mineral pigments, organic pigments and mixtures thereof.

By «pigments» it is meant white or coloured particles, mineral or organic, insoluble in an aqueous solution, intended to colour and/or opacify the resulting deposit. Mineral pigments, organic pigments can be cited as well as composite pigments i.e. pigments containing mineral and/or organic materials).

Among «mineral pigments», as examples, mention can be made of titanium dioxide (rutile or anatase), optionally surface-treated; black, yellow, red and brown iron oxides; manganese violet; ultramarine blue; chromium oxide, hydrated chromium oxide and iron blue.

For lip compositions, as examples mention can be made of titanium dioxide; black, yellow, red and brown iron oxides and manganese violet.

Among «organic pigments», mention can be made for example of pigments D & C red no 19; D & C red no 9; D & C Red no 22; D & C Red no 21; D & C Red no 28; D & C Yellow no 6; D & C orange no 4; D & C orange no 5; D & C Red no 27; D & C red no 13; D & C Red no 7; D & C Red no 6; D & C Yellow no 5; D & C Red no 36; D & C Red no 33; D & C orange no 10; D & C yellow no 6; D & C Red no 30; D &C red no 3; D &C Blue 1; carbon black and cochineal-based carmine lakes.

In particular, the coloring material(s) are contained in the composition in an amount ranging from 2% to 30% by weight, preferably 4% to 15% by weight relative to the total weight of the composition.

Galenic Form

In one particular and preferred embodiment, the composition of the invention is an anhydrous composition.

By «anhydrous», it is particularly meant that water is preferably not added to the compositions but may be present in trace form in the different compounds used in the compositions. In particular, the composition of the invention comprises less than 4% by weight of water, preferably less than 3%, more preferably less than 2%, further preferably less than 1% and still further preferably less than 0.5% by weight of water, relative to the total weight of said composition, and is even fully free of water.

In one particular embodiment, the composition is a semi-solid composition such as previously defined.

In another embodiment, the composition of the invention is a solid composition.

The composition of the invention is a makeup and/or care composition for keratin material, in particular a makeup and/or care composition for the skin and/or lips, preferably the lips.

As skin makeup composition, particular mention can be made of a solid foundation, eye shadow, blush, eye liner, eye pencil or cake mascara.

As lip makeup composition, particular mention can be made of a lipstick, lip contour pencil or lip balm.

In one particular and preferred embodiment, it is a solid, makeup composition for the lips, in particular a lipstick.

Cosmetic Method

The invention also concerns a cosmetic method for the care and/or makeup of keratin material, comprising the application to said keratin material, in particular to the skin and/or lips, of a composition of the invention.

The composition applied to the lips is preferably a solid, makeup composition for the lips, in particular a lipstick.

The method of the invention is in particular a makeup method for lips, intended to deposit on said lips a glossy film having long-lasting gloss and colour.

The invention will now be illustrated in the following nonlimiting examples. Percentages are expressed as weight percentages relative to the total weight of the composition unless otherwise stated.

EXAMPLES

Example 1: Selection of an Oil to be Associated with the Phenyl Silicone Oil 1.1 Behaviour of Binary Mixtures The Applicant has evaluated the ability of a phenyl silicone oil (Belsil PDM1000) to mix or not mix with various compounds and hydrocarbon or silicone oils.

With a binary mixture of non-miscible oils, a possible separation effect is observed into several strata (also called 'demixing'). For this purpose, the mixture of the two compounds or oils (BELSIL PDM000+Oil X) was heated to 80° C. for 15 minutes under agitation. The mixture was packaged in a transparent glass bottle. The mixture was observed at time TO then after a standing time of 24 hours:

The results are given in following Table 1:

BINARY MIXTURES: OIL X %/(100−X) % BELSIL PDM-1000)

TABLE 1

| X | INCI | 25% X in binary mixture | 75% X in binary mixture |
|---|---|---|---|
| Lusplan DD-DA 7 | Dimer dilinoleyl Dimer dilinoleate | ++ | ++ |
| Hailucent ISDA MB | Polyglyceryl-2-Isostearate/Dimer dilinoleate copolymer | ++ | ++ |
| PH-1555 HRI | Trimethyl Pentaphenyl Trisiloxane | 0 | ++ |
| Mirasil C-DPDM | Polydimethyldiphenylpolysiloxane + Dimethicone/vinyl Dimethicone crosspolymer | + | + |

TABLE 1-continued

| X | INCI | 25% X in binary mixture | 75% X in binary mixture |
|---|---|---|---|
| PTIS | Pentaerythrityl Tetraisostearate | ++ | ++ |
| Floralyn New Process | Methyl Hydrogenated Rosinate | 0 | 0 |
| Salacos 6318V | Trimethylolpropane Triisostearate | + | + |
| Salacos 43V | Polyglyceryl-2-Triisostearate | + | + |
| Salacos 222 | Diisostearyl Malate | 0 | ++ |
| Salacos 182 V | Sorbitan Sesquiisostearate | ++ | ++ |
| Phenyltrimethicone 30 CPS | Phenyltrimethicone | 0 | 0 |
| Isofol 20 | Octyldodecanol | ++ | ++ |
| Silshine 151 | Phenylpropyldimethylsiloxysilicate | 0 | ++ |
| BHA-free castor oil | Castor oil | ++ | ++ |
| KF-54 HV | Diphenyl Dimethicone | ++ | ++ |
| KF-56 A | Diphenylsiloxy Phenyl Trimethicone | 0 | 0 |

KEY:
0 transparent phase
+ cloudy phase
++ two phases

For test 1.2 only those oils, for which a demixing effect (separation) with the phenyl silicone oil (Belsil PDM1000) was observed, were retained for their 'gloss' effect and then evaluated for 'non-transfer' of colour.

1.2 Evaluation of Demixing and Non-Transfer Effect

The selected oils were used to prepare a coloured test formula comprising the phenyl silicone oil and also pigments.

The formula had the following composition (weight %):

TABLE 2

| INCI | Weight % |
|---|---|
| OIL X | 58.5 |
| Phenyl silicone oil (BELSIL PDM-1000) | 37.5 |
| Pigments | 4.0 |

The above test formula was packaged in a bottle. The test formula showed phase separation on standing having regard to the non-miscibility of the oils. It must therefore be shaken before the application step to the lips.

The behaviour of the test formula when applied to the lips was evaluated in vivo by a panel of experts: namely the onset of a transparent film on the surface of the coloured film, and the ability of this film to prevent colour transfer ('non-transfer' effect).

TABLE 3

| X | INCI | Evaluation |
|---|---|---|
| Lusplan DD-DA 7 | Dimer dilinoleyl Dimer dilinoleate | X |
| Hailucent ISDA MB | Polyglyceryl-2-Isostearate/Dimer dilinoleate copolymer | X |
| PTIS | Pentaerythrityl Tetraisostearate | X |
| Salacos 182 V | Sorbitan Sesquiisostearate | X |
| Isofol 20 | Octyldodecanol | OK |
| BHA-free castor oil | Castor oil | X |
| KF-54 HV | Diphenyl Dimethicone | X |

Evaluation of oil demixing effect and non-transfer of film colour

The demixing effect was observed on the lips after application of the film, and non-transfer of colour was evaluated by applying a substrate (e.g. a finger or paper handkerchief) to the lips several times at a few minutes interval.

It was surprisingly ascertained that octyldodecanol, a C8-C30 fatty alcohol, was the only oil among those tested which allows the formation of a transparent film on the surface of the coloured film (gloss effect), without colour transfer (non-transfer effect).

Example 2: Selection of Film-Forming Agents

The Applicant tested several film-forming agents (resins or polymers) to identify those which could form a homogeneous coloured film whilst maintaining the phenomenon of demixing related to the presence of non-miscible oils. By 'homogeneous film', it is meant a film which spreads homogeneously over the lips and gives a smooth finish of homogeneous colour, without any surface or colour irregularities.

2.1 Ability to Form a Homogeneous Film

Another test formula was prepared according to Table 4 below, comprising a film-forming agent and binary mixture selected in Example 1.

TABLE 4

| Ingredients | Weight % |
|---|---|
| Film-forming agent X | 12 |
| Octyldodecanol (ISOFOL 20) | 48 |
| Phenyl silicone oil (BELSIL PDM 1000) | 40 |

The test formula was applied to the lips. The homogeneity of the film was evaluated once the formula had been applied to the lips (Table 5)

TABLE 5

| X | INCI | Evaluation |
|---|---|---|
| Unifilma HVY | Dextrin Isostearate | ++ |
| Silicone gum | Silicone gum | 0 |
| Technol SD | Phytosterols | ++ |
| Ethocel std 7 Premium | Ethylcellulose | + |
| Candelilla Resin E-2 | *Euphorbia Cerifera* Extract (resin) | ++ |
| Kahlresin 6723 | *Shorea Robusta* Resin/ Octyldodecanol | ++ |

KEY:
++ Homogeneous film
+ Non-homogenous film
0 No film formation

For test 2.2, film-forming agents were selected which produce a homogeneous film on the lips.

2.2 Evaluation of Demixing and Non-Transfer Effect

A panel of experts again evaluated the behaviour of a formula coloured with pigments such as defined in Table 6, comprising a film-forming agent selected at 2.1.

TABLE 6

| Ingredients | Weight % |
|---|---|
| Film-forming agent X | 46.7 |
| Octyldodecanol (ISOFOL 20) | 11.8 |
| Phenyl silicone oil (BELSIL PDM 1000) | 37.5 |
| Pigments | 4 |

The above formula was shaken, if necessary, before application to the lips.

Using the same method as in 1.2, the behaviour was evaluated of the coloured formula with film-forming agent (Table 6). The results of evaluation of demixing and of non-transfer of colour are given in Table 7 below:

TABLE 7

| X | INCI | Evaluation |
|---|---|---|
| Unifilma HVY | Dextrin Isostearate | OK |
| Technol SD | Phytosterols | X |
| Candelilla Resin E-2 | *Euphorbia Cerifera* Extract (resin) | X |
| Kahlresin 6723 | *Shorea Robiusta* Resin/ Octyldodecanol | X |

It follows from this study that solely dextrin isostearate (branched dextrin ester) allows the desired properties to be obtained of gloss, non-transfer of colour and homogeneity of the makeup film.

Example 3: Selection of Long-Wear Polymers

After Examples 1 and 2 above, it was sought to improve the long-wear of the coloured film obtained with the composition of the invention, whilst maintaining a gloss effect related to the phenomenon of demixing ascertained above.

A composition was prepared according to Table 8, containing both the film-forming agent and the oil selected in the preceding examples:

TABLE 8

| Description | Weight % |
|---|---|
| Octyldodecanol (ISOFOL 20) | 13.5 |
| Dextrin isostearate 'UNIFILMA HVY) | 35 |
| LONG-WEAR POLYMER X | 10 |
| Pigments | 4 |
| Phenyl silicone oil (BELSIL PDM-1000) | 37.5 |

The pigments were ground in the presence of octyldodecanol. This pigment phase was heated to 95° C.

Separately, the dextrin isostearate was dispersed in octyldodecanol at 95° C. in a Rayneri mixer. After homogenization, the phenyl silicone oil was added.

The two previously prepared phases were mixed and homogenized under heat.

The long-wear polymer X was added to the composition obtained at the preceding step.

The composition was poured into suitable packaging and cooled.

The properties were evaluated of the different prepared compositions following the protocol below:

The product was applied to the lips with the applicator if the product was semi-pasty, and directly in stick form if the product was solid.

a—Evaluation at T0

After depositing the film of the composition on the lips, a time of 5 minutes was waited before applying a finger lightly to lips to evaluate tackiness of the film and to verify non-transfer of the coloured film. A photo was taken of the made-up lips for visual evaluation of gloss at T0.

b—Evaluation at T12 h

A finger was lightly applied to the lips to evaluate tackiness and to verify non-transfer of the coloured film at T2 h.

A photo was taken of the made-up lips to evaluate gloss and to compare this gloss with the gloss observed at T0.

The results are given in following Table 9:

TABLE 9

| NAME | INCI | Demixing and non-transfer effect | Evaluation tackiness and gloss | Comments |
|---|---|---|---|---|
| KP 561-P | Acrylates/Stearyl Acrylate/Dimethicone methacrylate copolymer | 2 | 0 | Moderately glossy film |
| Unimer U-6 | Triacontanyl PVP | 1 | | |
| OM-4 | Acrylates copolymer/Isoparaffin | 0 | | |
| Regalite R1100 | Hydrogenated styrene/Methyl styrene/Indene copolymer | 2 | − | Scarcely glossy film |
| ULTRAHOLD 8 in oil | Acrylates/1-Butylacrylamide copolymer and hydrogenated polyisobutene | 2 | + | Very glossy film |
| KOBOGUARD HRPC | Hydrogenated polycyclopentadiene and polyethylene and *copernicia cerifera* (carnauba) wax and tocopherol | 1 | | |
| UNIMER U-1946 | VP/Hexadecene copolymer and octydodecanol | 1 | | |
| KF-7312 J | Trimethylsiloxysilicate and cyclopentasiloxane | 1 | | |
| ANTARON V220 F | Eicosene vinylpyrrolidone copolymer | 2 | + | Non-tacky film |
| TEGO SP 13-1 | poly C10-30 alkyl acrylate | 2 | 0 | Moderately glossy film |
| ANTARON V216 | Polyvinylpyrrolidone/1-hexadecene) | 0 | | |
| KP-550 | Isododecane (and) Acrylates/Dimethicone copolymer | 1 | | |

KEY:
Effect (demixing and non-transfer)
Satisfactory effect: 2
Insufficient performance: 1
No effect: 0
Evaluation (tackiness and gloss) for formulas with satisfactory demixing and non-transfer effect (score 2):
− insufficient
0 moderate
+ satisfactory It is ascertained that the tested long-wear polymers do not all exhibit the same behaviour when associated in a composition of the invention.

A certain number thereof do not allow the effect of the invention to be obtained i.e. the onset of a transparent film on the surface of the applied film imparting gloss and non-transfer of colour.

Diverging evaluations of performance were given by a panel of experts in terms of tackiness, gloss and long-wear.

To obtain optimal performance in a composition of the invention, preference is given to the use of an eicosene vinylpyrrolidone copolymer and/or a copolymer of acrylates/t-Butylacrylamide.

Example 4: Compositions of the Invention

The following compositions are illustrated with long-wear polymers, but it is also possible to prepare compositions without a long-wear polymer (q.s. for oils, resin and waxes) and to obtain gloss and non-transfer performance that is fully acceptable.

The use of long-wear polymers further improves the lasting property of said compositions.

The following compositions comprising long-wear polymers were prepared following the operating mode below:

The resin (branched dextrin ester) and a long-wear polymer (acrylate/butyl acrylamide copolymer) are added to part of the octyldodecanol at 95° C. under agitation.

After homogenization, a second long-wear polymer (VP/eicosene copolymer) is added and left under agitation 30 min.

The addition is then made of the waxes and agitation continued 20 min.

The pigments are ground in the remaining octyldodecanol.

This pigment phase is added to the remainder of the formula and homogenized.

Phenyl silicone oil (Belsil PDM1000) is added to the preparation under heat and agitation for at least 20-30 min.

The addition is then made of the oils and semi-solid fatty substances, and agitation continued for 15 min.

After adding the powder fillers, agitation is continued for 20-30 min.

Finally, the isododecane is added and left to homogenize for no more than 2 minutes.

The composition is packaged in a suitable pack.

TABLE 10

4-1 Semi-pasty composition for the lips

| Phases | Compounds (INCI name) | Weight % |
|---|---|---|
| A | Octyldodecanol | 1.5 |
| | Dextrin isostearate (Unifilma HVY) | 10 |
| | Acrylates/t-Butylacrylamide copolymer (ULTRAHOLD 8) and hydrogenated polyisobutene | 3% a.m. |
| B1 | VP/eicosene copolymer (Antaron V 220 F) | 10 |
| B2 | Candelilla wax | 4 |
| C | Pigments | 11 |
| | Octyldodecanol | 17 |
| D1 | Trimethyl siloxyphenyl dimethicone (Belsil PDM1000) | 19 |
| D2 | Trimethyl pentaphenyl trisiloxane (Dow Corning PH-1555 HRI) | 5 |
| E | Caprylic/capric/myristic/stearic triglyceride | 3 |
| F | Cellulose | 3 |
| G | Isododecane | q.s. 100 |

The composition was prepared following the above operating mode and packaged in a glass tube-type pack for gloss. Its visual appearance was homogeneous.

Applied to the lips, the composition leaves a glossy film. The lasting property of the gloss film is improved and lasts all day long whilst remaining comfortable.

4-2 Solid Composition for the Lips (Anhydrous Stick)

TABLE 11

| Phases | Compounds (INCI name) | Weight % |
|---|---|---|
| A | Octyldodecanol | 2 |
| | Dextrin isostearate (Unifilma HVY) | 12.5 |
| | Acrylates/t-Butylacrylamide copolymer (ULTRAHOLD STRONG) and hydrogenated polyisobutene | 3.5 |
| B1 | VP/eicosene copolymer (Antaron V 220 F) | 12.5 |
| B2 | Candelilla wax | 9 |
| C | Pigments | 2.5% |
| | Octyldodecanol | 3 |
| D1 | Trimethyl siloxyphenyl dimethicone (Belsil PDM1000) | 32 |
| D2 | Trimethyl pentaphenyl trisiloxane (Dow Corning PH-1555 HRI) | 7 |
| E | Caprylic/capric/myristic/stearic triglyceride | 3 |
| F | Cellulose | 3 |
| | Silica | 1.5 |
| G | Isododecane | q.s. 100 |

The composition was prepared following the operating mode described above and packaged in a stick-type pack for lipstick. The visual appearance of the stick was homogeneous.

As with composition 4.1, the composition leaves a glossy film on the lips. The long-wear property of the film gloss is improved to last throughout the day, whilst remaining comfortable.

4-3 Solid Composition for the Lips (Anhydrous Stick)

TABLE 12

| Phases | Compounds (INCI name) | Weight % |
|---|---|---|
| A | Octyldodecanol | 10.5 |
| | Dextrin isostearate (Unifilma HVY) | 28.5 |
| B | Candelilla wax | 10 |
| C | Pigments | 10.5 |
| D1 | Trimethyl siloxyphenyl dimethicone (Belsil PDM1000) | 32.0 |
| D2 | Trimethyl pentaphenyl trisiloxane (Dow Corning PH-1555 HRI) | 7.0 |
| F | Cellulose | 3.0 |
| | Silica | 1.5 |
| G | Isododecane | q.s 100% |

The composition, without long-wear polymer, was prepared following the operating mode described above and packaged in a stick-type pack for lipstick. The visual appearance of the solid composition was homogeneous.

The composition leaves a glossy film on the lips. Film gloss is improved by means of the compounds of phases A, D1 and D2, to last throughout the day, whilst remaining comfortable.

4-4 Solid Composition for the Lips (Anhydrous Stick)

TABLE 13

| Compounds (INCI name) | Weight % |
|---|---|
| Octyldodecanol | 4 |
| Dextrin isostearate (Unifilma HVY) | 12 |
| VP/eicosene copolymer (Antaron V 220 F) | 11 |
| Candelilla wax | 11 |
| Pigments | 2.5 |
| Trimethyl siloxyphenyl dimethicone (Belsil PDM1000) | 32 |
| Caprylic/capric/myristic/stearic triglyceride | 8 |
| Cellulose | 3.5 |
| Silica | 1.5 |
| Isododecane | q.s. 100 |

The composition leaves a glossy film on the lips, that is comfortable with good staying power.

The invention claimed is:

1. A solid cosmetic composition comprising, in a physiologically acceptable medium, an oily phase and at least:

a) trimethylsiloxyphenyl dimethicone in an amount ranging from 15 to 35% by weight relative to the total weight of the composition, b) octyldodecanol in an amount ranging from 2 to 5% by weight relative to the total weight of the composition, c) dextrin isostearate in an amount ranging from 10 to 18% by weight relative to the total weight of the composition, wherein it further comprises a liposoluble polymer in a total amount ranging from 10% to 15% by weight relative to the total weight of the composition selected from the group consisting of:

(i) copolymers of acrylates and acrylamide, (ii) copolymers of vinylpyrrolidone (VP) and alkene having between 18 and 30 carbon atoms, and (iii) mixtures thereof, and d) a candelilla wax in a total amount ranging from 3% to 15% by weight relative to the total weight of the composition.

2. The cosmetic composition according to claim 1, wherein the liposoluble polymer is selected from among a copolymer of acrylates and acrylamide and a copolymer of vinylpyrrolidone (VP) and alkene having at least 20 carbon atoms.

3. The cosmetic composition according to claim 1, wherein it is an anhydrous composition.

4. The composition according to claim 1, wherein in that it comprises at least the following compounds:

trimethylsiloxyphenyl dimethicone octyldodecanol dextrin isostearate and a VP/eicosene copolymer.

5. The composition according to claim 1, wherein it further comprises an additional ingredient selected from among additional oils, fillers, pasty fatty substances, gelling agents, coloring materials, and mixtures thereof.

6. The cosmetic composition according to claim 1, wherein it is a makeup and/or care composition for the skin and/or lips.

7. The cosmetic composition according to claim 1, wherein the composition is a lip paint, gloss, or lipstick.

8. A cosmetic method comprising the application to keratin material, of a cosmetic composition comprising, in a physiologically acceptable medium, an oily phase and at least:

a) trimethylsiloxyphenyl dimethicone in an amount ranging from 15 to 35% by weight relative to the total weight of the composition, b) octyldodecanol in an amount ranging from 2 to 5% by weight relative to the total weight of the composition, c) dextrin isostearate in an amount ranging from 10 to 18% by weight relative to the total weight of the composition, wherein it further comprises a liposoluble polymer in a total amount ranging from 10% to 15% by weight relative to the total weight of the composition selected from the group consisting of:

(i) copolymers of acrylates and acrylamide, (ii) copolymers of vinylpyrrolidone (VP) and alkene having between 18 and 30 carbon atoms, and (iii) mixtures thereof, and d) a candelilla wax in a total amount ranging from 3% to 15% by weight relative to the total weight of the composition.

9. The cosmetic method according to claim 8, wherein the cosmetic composition is applied onto skin.

10. The cosmetic method according to claim 8, wherein the cosmetic composition is applied onto lips.

* * * * *